(12) United States Patent
Bonni et al.

(10) Patent No.: US 7,786,090 B2
(45) Date of Patent: Aug. 31, 2010

(54) METHODS AND COMPOSITIONS FOR TREATING AND PREVENTING NEUROLOGIC DISORDERS

(75) Inventors: Azad Bonni, Brookline, MA (US); Esther B. E. Becker, Oxford (GB)

(73) Assignee: President and Fellows of Harvard College, Cambridge, MA (US)

( * ) Notice: Subject to any disclaimer, the term of this patent is extended or adjusted under 35 U.S.C. 154(b) by 475 days.

(21) Appl. No.: 11/713,302

(22) Filed: Mar. 1, 2007

(65) Prior Publication Data

US 2007/0282017 A1 Dec. 6, 2007

Related U.S. Application Data

(60) Provisional application No. 60/778,536, filed on Mar. 1, 2006.

(51) Int. Cl.
*A61K 48/00* (2006.01)
*C07H 21/02* (2006.01)
*C07H 21/04* (2006.01)

(52) U.S. Cl. .................. 514/44; 536/23.1; 536/24.5

(58) Field of Classification Search .................. None
See application file for complete search history.

(56) References Cited

U.S. PATENT DOCUMENTS

| | | | | |
|---|---|---|---|---|
| 3,625,214 | A | 12/1971 | Higuchi | 128/260 |
| 4,789,734 | A | 12/1988 | Pierschbacher | 530/395 |
| 4,925,673 | A | 5/1990 | Steiner et al. | 424/455 |
| 5,954,687 | A | 9/1999 | Baudino | 604/48 |

FOREIGN PATENT DOCUMENTS

WO  WO 99/63931  12/1999

OTHER PUBLICATIONS

Ryo et al., Stable Suppression of Tumorigenicity by Pin1-Targeted RNA Interference in Prostate Cancer, 2005, Clin Cancer Res, 11(20), 2005.*
Holzer et al., Inverse Association of Pin1 and tau accumulation in Alzheimer's disease hippocampus, 2002, Acta Neuropathol, 104, pp. 471-481.*
Scherer et al., Approaches for the sequence-specific knockdown of mRNA, 2003, Nat. Biotechnol., 21(12), pp. 1457-1465.*
Mahato et al., Modulation of gene expression by antisense and antigene oligodeoxynucleotides and small interfering RNA, Jan. 2005, Expert Opinion on Drug Delivery, vol. 2, No. 1, pp. 3-28.*
Zhang et al., Targeted Gene Silencing by Small Interfering RNA-Based Knock-Down Technology, 2004, Current Pharmaceutical Biotechnology, vol. 5, p. 1-7.*
Accession No. AAC50492, May 1996.
Accession No. BAA87038, Nov. 1999.
Becker et al., "Characterization of the c-Jun-Terminal Kinase-Bim$_{EL}$ Signaling Pathway in Neuronal Apoptosis", *J. Neurosci.*, 24(40):8762-8770 (2004).
Becker et al., "Pin1 Mediates Neural-Specific Activation of the Mitochondrial Apoptotic Machinery", *Neuron*, 49:655-662 (2006).
Chao et al., "Juglone, an Inhibitor of the Peptidyl-Prolyl Isomerase Pin1, also directly blocks Transcription", *Nuc. Acids Res.*, 29(3):767-773 (2001).
Daum et al., "Aryl Indanyl Ketones: Efficient Inhibitors of the Human Peptidyl Prolyl *cis/trans* Isomerase Pin1", *Angew. Chem. Int. Ed.*, 45:7454-7458 (2006).
Etzkorn, F., "Synthesized Molecules Studied as Weapon to Stop Cell Division in Cancer Cells", *EurekAlert*, http://www.eurkalert.org/pub_releases/2004-08/vt-sms081604.php, 3 pages (2004).
Gregoriadis, "Liposomes", *Drug Carriers Biol. Med.*, (Academic Press), p. 287-341 (1979).
Joliot et al., "Antennapedia Homobox Peptide Regulates Neural Morphogenesis", *Proc. Natl. Acad. Sci. USA*, 88:1864-1868 (1991).
Konishi et al., "Cdc2 Phosphorylation of BAD Links the Cell Cycle to the Cell Death Machinery", *Mol. Cell*, 9:1005-1016 (2002).
Konishi et al., "Cdh 1-APC Controls Axonal Growth and Patterning in the Mammalian Brain", *Science*, 303:1026-1030 (2004).
Kotin et al., "Site-Specific Integration by Adeno-Associated Virus", *Proc. Natl. Acad. Sci. USA*, 87:2211-2215 (1990).
Lu et al., "Gene Transfer into Hepatocytes Using a Defective Herpes Simplex Viral Vector", Abstracts of the Meeting on Gene Therapy, Sep. 22-26, Cold Spring Harbor Laboratory, Cold Spring Harbor, N.Y., Abstract, p. 66 (1992).
Morsey et al., "Efficient Adenoviral Gene Transduction in Human and Mouse Hepatocytes In Vitro and in Mouse Liver In Vivo",*J. Cell. Biochem.*, Abstract SZ 109, Supp. 17E:226 (1993).
Rosenberg et al., "Gene Transfer into Humans—Immunotherapy of Patients with Advanced Melanoma, Using Tumor-Infiltrating Lymphocytes Modified by Retroviral Gene Transduction", *N. Eng. J. Med.*, 323(9):570-578 (1990).
Rubinson et al., "A Lentivirus-Based System to Functionally Silence Genes in Primary Mammalian Cells, Stem Cells and Transgenic Mice by RNA Interference", *Nat. Gen.*, 33:401-406 (2003).
Ryo et al., "Regulation of NF-κB Signaling by Pin1-Dependent Prolyl Isomerization and Ubiquitin-Mediated Proteolysis of p65/RelA", *Mol. Cell.*, 12:1413-1426 (2003).
Uchida et al., "Pin1 and Par14 Peptidyl Prolyl Isomerase Inhibitors Block Cell Proliferation", *Chem. Biol.*, 10:15-24 (2003).
Vandre, D., "Inhibition of the Pin1 Prolyl Isomerase: A Novel Approach for DNA Checkpoint Abrogation in Breast Cancer Cell Lines", *Storming Media*, Pentagon Reports, http://www.stromingmedia.us/08/0840/A084004.html, 2 pages (2006).
Vandre, D., "Inhibition of the Pin1 Prolyl Isomerase: A Novel Approach for DNA Checkpoint Abrogation in Breast Cancer Cell Lines", Report, Award Number: DAMD17-00-1-0645, U.S. Army Medical Research and Material Command Fort Detrick, Maryland, 19 pages (2001).
Wildemann et al., "Nanomolar Inhibitors of teh Peptidyl Prolyl Cis/Trans Isomerase Pin1 From Combinatorial Peptide Libraries", *J. Med. Chem.*, 49:2147-2150 (2006).
Pastorino et al. "The Prolyl Isomerase Pin1 Regulates Amyloid Precursor Protein Processign and Amyloid-β Production" *Nature*, 440(23):528-534 (2006).

* cited by examiner

*Primary Examiner*—Amy Bowman
(74) *Attorney, Agent, or Firm*—Mintz Levin Cohn Ferris Glovsky and Popeo, P.C.; Ingrid A. Beattie, Esq.

(57) ABSTRACT

The present invention provides methods for treating or reducing neurologic disorders.

6 Claims, 8 Drawing Sheets

| | |
|---|---|
| Pin1 RNAi targeted sequence | GAIGACICUGIGGUIGCCIUUCIAGCIA SEQ ID NO: 7 |
| Pin1 Rescue sequence | GAIGAUCUCIGGCIGCGIUUUIAGTIA SEQ ID NO: 8 |
| Protein Sequence | L G A F S R SEQ ID NO: 9 |

SEQUENCE LISTING

<160> NUMBER OF SEQ ID NOS: 11

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
gagacctggg tgccttcagc a                                                    21

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Phe Tyr Ser Pro Arg
 1               5

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)
<223> OTHER INFORMATION: Phospho-Ser

<400> SEQUENCE: 3

Tyr Gly Arg Lys Lys Arg Arg Gln Arg Arg Trp Phe Tyr Ser Pro
 1               5                  10                  15

Arg

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(N-biotinoyl)
<220> FEATURE:
<221> NAME/KEY: MOD_RES
<222> LOCATION: (4)
<223> OTHER INFORMATION: Bth
<220> FEATURE:
<221> NAME/KEY: MOD_RES
<222> LOCATION: (5)
<223> OTHER INFORMATION: D-Thr(PO3H2)
<220> FEATURE:
<221> NAME/KEY: MOD_RES
<222> LOCATION: (6)
<223> OTHER INFORMATION: Pip
<220> FEATURE:
<221> NAME/KEY: MOD_RES
<222> LOCATION: (7)
<223> OTHER INFORMATION: Nal

<400> SEQUENCE: 4

Lys Ala Ala Xaa Thr Xaa Xaa Gln
 1               5

<210> SEQ ID NO 5
<211> LENGTH: 5
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Thr(PO3H2)
<220> FEATURE:
<221> NAME/KEY: MOD_RES
<222> LOCATION: (3)
<223> OTHER INFORMATION: Pip
<220> FEATURE:
<221> NAME/KEY: MOD_RES
<222> LOCATION: (4)
<223> OTHER INFORMATION: Nal

<400> SEQUENCE: 5

Phe Thr Xaa Xaa Gln
 1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Phospho-Ser

<400> SEQUENCE: 6

Trp Phe Tyr Ser Pro Arg Leu Lys Lys
 1               5

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gagaccuggg ugccuucagc a                                          21

<210> SEQ ID NO 8
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 8
gagaucucgg cgcguuuagt a                                          21

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

```
Leu Gly Ala Phe Ser Arg
  1               5
```

<210> SEQ ID NO 10
<211> LENGTH: 163
<212> TYPE: PRT
<213> ORGANISM: Homo sapiens

<400> SEQUENCE: 10

```
Met Ala Asp Glu Glu Lys Leu Pro Pro Gly Trp Glu Lys Arg Met Ser
  1               5                  10                  15

Arg Ser Ser Gly Arg Val Tyr Tyr Phe Asn His Ile Thr Asn Ala Ser
                 20                  25                  30

Gln Trp Glu Arg Pro Ser Gly Asn Ser Ser Gly Gly Lys Asn Gly
             35                  40                  45

Gln Gly Glu Pro Ala Arg Val Arg Cys Ser His Leu Leu Val Lys His
         50                  55                  60

Ser Gln Ser Arg Arg Pro Ser Ser Trp Arg Gln Glu Lys Ile Thr Arg
 65                  70                  75                  80

Thr Lys Glu Glu Ala Leu Glu Leu Ile Asn Gly Tyr Ile Gln Lys Ile
                 85                  90                  95

Lys Ser Gly Glu Glu Asp Phe Glu Ser Leu Ala Ser Gln Phe Ser Asp
            100                 105                 110

Cys Ser Ser Ala Lys Ala Arg Gly Asp Leu Gly Ala Phe Ser Arg Gly
            115                 120                 125

Gln Met Gln Lys Pro Phe Glu Asp Ala Ser Phe Ala Leu Arg Thr Gly
        130                 135                 140

Glu Met Ser Gly Pro Val Phe Thr Asp Ser Gly Ile His Ile Ile Leu
145                 150                 155                 160

Arg Thr Glu
```

<210> SEQ ID NO 11
<211> LENGTH: 165
<212> TYPE: PRT
<213> ORGANISM: Mus musculus

<400> SEQUENCE: 11

```
Met Ala Asp Glu Glu Lys Leu Pro Pro Gly Trp Glu Lys Arg Met Ser
  1               5                  10                  15

Arg Ser Ser Gly Arg Val Tyr Tyr Phe Asn His Ile Thr Asn Ala Ser
                 20                  25                  30

Gln Trp Glu Arg Pro Ser Gly Ser Thr Val Gly Gly Ser Ser Lys
             35                  40                  45

Asn Gly Gln Gly Glu Pro Ala Lys Val Arg Cys Ser His Leu Leu Val
 50                  55                  60

Lys His Ser Gln Ser Arg Arg Pro Ser Ser Trp Arg Gln Glu Lys Ile
 65                  70                  75                  80

Thr Arg Ser Lys Glu Glu Ala Leu Glu Leu Ile Asn Gly Tyr Ile Gln
                 85                  90                  95

Lys Ile Lys Ser Gly Glu Glu Asp Phe Glu Ser Leu Ala Ser Gln Phe
            100                 105                 110

Ser Asp Cys Ser Ser Ala Lys Ala Arg Gly Asp Leu Gly Pro Phe Ser
            115                 120                 125

Arg Gly Gln Met Gln Lys Pro Phe Glu Asp Ala Ser Phe Ala Leu Arg
        130                 135                 140
```

```
Thr Gly Glu Met Ser Gly Pro Val Phe Thr Asp Ser Gly Ile His Ile
145                 150                 155                 160

Ile Leu Arg Thr Glu
                165
```

METHODS AND COMPOSITIONS FOR TREATING AND PREVENTING NEUROLOGIC DISORDERS

RELATED U.S. APPLICATION

This application claims priority to U.S. Ser. No. 60/778,536 filed Mar. 1, 2006, which is incorporated herein by reference in its entirety.

STATEMENT AS TO FEDERALLY SPONSORED RESEARCH

This invention was funded in part by the U.S. Government under grant number NS41021 awarded by the National Institute of Neurological Disorders and Stroke (NINDS). The Government has certain rights in the invention.

BACKGROUND OF THE INVENTION

Apoptosis of neurons is a fundamental process in the development of the nervous system and contributes to the pathogenesis of several neurologic disorders. Since neurons are postmitotic cells that last the entire lifespan of an organism, specific mechanisms have evolved to regulate apoptosis in neurons. Since the mechanisms underlying neuron-specific mechanisms of apoptosis remains poor, there is a dearth of treatment modalities for neurologic disorders that involve excessive neurodegenerative disorders.

SUMMARY OF THE INVENTION

The invention provides a method of reducing neural cell apoptosis by contacting a neural cell (e.g., granule neuron) with an agent that reduces the level or activity of the prolyl isomerase Pin1. Inhibitors such as substrate analogs and RNA interference vectors or products thereof preferentially reduce apoptosis in neural cells compared to non-neural cells. For example, the inhibitor reduces apoptosis at least 20%, 50%, 100%, 2 fold, 5-fold and up to ten fold in neural cells as compared to non-neural cells. By reducing neural cell apoptosis, this agent is useful for treating or preventing neurologic or neurodegenerative disorders including Alzheimer's disease, multiple sclerosis, Parkinson's disease, amyotrophic lateral sclerosis, stroke, cerebral ischemic disease, Hunting-ton's disease, spinal muscular atrophy, stroke, brain trauma, spinal cord injury, diabetic neuropathy, and other neurodegenerative diseases. For example, the agent reduces apoptosis by reducing binding of Pin1 to $BIM_{EL}$, e.g., a $BIM_{EL}$ domain contain a phosphorylated serine residue at amino acid position 65 of $BIM_{EL}$. Exemplary agents are small molecule inhibitors and RNA interfering agents. A small molecule inhibitor is a compound that is less than 2000 daltons in mass. The molecular mass of the inhibitory compounds is preferably less than 1000 daltons, more preferably less than 600 daltons, e.g., the compound is less than 500 daltons, 400 daltons, 300 daltons, 200 daltons, or 100 daltons. In some embodiments, the inhibitor is a peptide. For example, the peptide is at least 8, 10, 20, 30, 40 residues in length and inhibits binding of endogenous Pin1 to $BIM_{EL}$. In other embodiments, the inhibitor is not a peptide or proteinaceous in nature.

The invention also provides methods for identifying a candidate compound for reducing or preventing apoptosis in a neural cell. These methods involve the steps of: (a) contacting a cell expressing a Pin1 gene with a candidate compound; and (b) measuring Pin1 gene expression or protein activity in the cell. A candidate compound that decreases the expression or the activity of Pin1 relative to such expression or activity in a cell that has not been contacted with the candidate compound is useful for reducing or preventing neural cell apoptosis. For example, the candidate compound reduces binding of Pin1 to $BIM_{EL}$, specifically phosphorylated Ser65 $BIM_{EL}$. Optionally, the Pin1 gene is a Pin1 fusion gene and the Pin1-expressing cell is a mammalian cell (e.g., a rodent or human cell). In other embodiments, step (b) involves the measurement of the level of Pin1 mRNA or protein.

Alternatively, the method involves the steps of: (a) contacting a Pin1 protein with a candidate compound; and (b) determining whether the candidate compound binds the Pin1 protein and/or reduces Pin1 activity. Candidate compounds that bind and reduce Pin1 activity are identified as compounds useful for reducing or preventing neural cell apoptosis. Preferably, the candidate compound reduces binding of Pin1 to $BIM_{EL}$, specifically the phosphorylated Ser65 $BIM_{EL}$.

In yet another screening approach, a method for identifying a candidate compound for reducing or preventing neural cell apoptosis involves the steps of: (a) contacting a Pin1 protein (e.g., human Pin1 protein) with a candidate compound; and (b) determining whether the candidate compound decreases binding of Pin1 to $BIM_{EL}$. The candidate compound is first contacted with Pin1, $BIM_{EL}$, or is simultaneously contacted with both proteins or fragments thereof, e.g., a fragment of $BIM_{EL}$ containing phosphorylated Ser65. Candidate compounds that decrease such binding reduce or prevent neural cell apoptosis.

In all foregoing aspects of the invention, candidate compounds identified as being useful for reducing or preventing neural cell apoptosis are useful to treat or prevent neural disorders.

By "reduce the expression or activity of Pin1" is meant to reduce the level or biological activity of Pin1 relative to the level or biological activity of Pin1 in an untreated control. The level or activity is preferably reduced by at least 10%, 20%, 30%, 40%, 50%, 60%, 70%, 80%, 90%, or 100%, relative to an untreated control. Since Pin1 binds and stabilizes $BIM_{EL}$, a reduction in the biological activity of Pin1 is, for example, a reduction in the activity of $BIM_{EL}$, in turn resulting in a reduction in apoptosis. For example, the binding interaction between Pin1 and $BIM_{EL}$ is reduced by at least 10%, 20%, 30%, 40%, 50%, 60%, 70%, 80%, 90%, or even 100% relative to an untreated control, thereby reducing apoptosis and ultimately treating or reducing neural or neurodegenerative disorders. Thus, as used herein, the term "activity" with respect to a Pin1 polypeptide includes any activity which is inherent to the naturally occurring Pin1 protein, such as binding and stabilizing $BIM_{EL}$, activation of neural apoptosis, or both, as detected by any standard method.

By "treating or preventing a neurologic disorder" is meant ameliorating any of the conditions or symptoms associated with the disorder before or after it has occurred including, for example, seizures, headaches, and memory loss. Alternatively, alleviating a symptom of a disorder may involve reducing visible areas of neuronal cell death relative to an untreated control. As compared with an equivalent untreated control, such reduction or degree of prevention is at least 5%, 10%, 20%, 40%, 50%, 60%, 80%, 90%, 95%, or 100% as measured by any standard technique. A patient who is being treated for a neurologic disorder is one who a medical practitioner has diagnosed as having such a condition. Diagnosis may be by any suitable means. Diagnosis and monitoring may involve, for example, detecting the presence of destroyed or dying neurons in a biological sample (e.g., tissue biopsy, blood test, or urine test), detecting the presence of amyloid plaques, detecting the level of a surrogate marker of the neurologic disorder in a biological sample, or detecting symptoms associated with the neurologic disorder. A patient in whom the development of a neurologic disorder is being prevented may or may not have received such a diagnosis. One in the art will understand that these patients may have been subjected to the same standard tests as described above or may have been identified, without examination, as one at high risk due to the presence of one or more risk factors (e.g., family history or genetic predisposition).

As used herein, by "Pin1" is meant a polypeptide that forms a complex with the $BIM_{EL}$ and is involved in various signaling pathways including mitochondrial apoptosis. The Pin1 proteins of the invention are substantially identical to the naturally occurring Pin1 (e.g., accession numbers AAC50492 (human PIN1 (SEQ ID NO: 10) and BAA87038 (murine PIN1 (SEQ ID NO: 11), the sequences of which are hereby incorporated by reference). Neurologic disorders are treated or prevented when Pin1 activity or expression is reduced by at least 5%, 10%, 20%, 30%, 40%, 50%, 60%, 70%, 80%, 90%, or 100% below control levels as measured by any standard method (e.g.,. Northern blot analysis).

By a "Pin1 gene" is meant a nucleic acid that encodes a Pin1 protein.

By "Pin1 fusion gene" is meant a Pin1 promoter and/or all or part of a Pin1 coding region operably linked to a second, heterologous nucleic acid sequence. In preferred embodiments, the second, heterologous nucleic acid sequence is a reporter gene, that is, a gene whose expression may be assayed; reporter genes include, without limitation, those encoding glucuronidase (GUS), luciferase, chloramphenicol transacetylase (CAT), green fluorescent protein (GFP), alkaline phosphatase, and beta-galactosidase.

By "substantially identical," when referring to a protein or polypeptide, is meant a protein or polypeptide exhibiting at least 75%, but preferably 85%, more preferably 90%, most preferably 95%, or even 99% identity to a reference amino acid sequence. For proteins or polypeptides, the length of comparison sequences will generally be at least 20 amino acids, preferably at least 30 amino acids, more preferably at least 40 amino acids, and most preferably 50 amino acids or the full length protein or polypeptide. Nucleic acids that encode such "substantially identical" proteins or polypeptides constitute an example of "substantially identical" nucleic acids; it is recognized that the nucleic acids include any sequence, due to the degeneracy of the genetic code, that encodes those proteins or polypeptides. In addition, a "substantially identical" nucleic acid sequence also includes a polynucleotide that hybridizes to a reference nucleic acid molecule under high stringency conditions.

By "high stringency conditions" is meant any set of conditions that are characterized by high temperature and low ionic strength and allow hybridization comparable with those resulting from the use of a DNA probe of at least 40 nucleotides in length, in a buffer containing 0.5 M $NaHPO_4$, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1× Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well known by those skilled in the art of molecular biology. See, e.g., F. Ausubel et al., Current Protocols in Molecular Biology, John Wiley & Sons, New York, N.Y., 1998, hereby incorporated by reference.

By "substantially pure" is meant a nucleic acid, polypeptide, or other molecule that has been separated from the components that naturally accompany it. Typically, the polypeptide is substantially pure when it is at least 60%, 70%, 80%, 90%, 95%, or even 99%, by weight, free from the proteins and naturally-occurring organic molecules with which it is naturally associated. For example, a substantially pure polypeptide may be obtained by extraction from a natural source, by expression of a recombinant nucleic acid in a cell that does not normally express that protein, or by chemical synthesis.

The term "isolated DNA" is meant DNA that is free of the genes which, in the naturally occurring genome of the organism from which the given DNA is derived, flank the DNA. Thus, the term "isolated DNA" encompasses, for example, cDNA, cloned genomic DNA, and synthetic DNA.

By "an effective amount" is meant an amount of a compound, alone or in a combination, required to reduce or prevent the neurologic disorder in a mammal. The effective amount of active compound(s) varies depending upon the route of administration, age, body weight, and general health of the subject. Ultimately, the attending physician or veterinarian will decide the appropriate amount and dosage regimen.

By a "candidate compound" is meant an agent to be evaluated as a Pin1 inhibitor. Candidate compounds may include, for example, peptides, polypeptides, synthetic organic molecules, naturally occurring organic molecules, nucleic acid molecules, peptide nucleic acid molecules, and components and derivatives thereof.

The term "pharmaceutical composition" is meant any composition, which contains at least one therapeutically or biologically active agent and is suitable for administration to the patient. Any of these formulations can be prepared by well-known and accepted methods of the art. See, for example, Remington: The Science and Practice of Pharmacy, $20^{th}$ edition, (ed. A. R. Gennaro), Mack Publishing Co., Easton, Pa., 2000.

The invention provides significant advantages over standard therapies for treatment, prevention, and reduction, or alternatively, the alleviation of one or more symptoms associated with neurologic disorders, because it preferentially targets neural cells compared to non-neural cells. In addition, the screening methods allow for the identification of therapeutics that modify the injury process rather than merely mitigating the symptoms.

Cited publications including sequences defined by GENBANK™ accession numbers are incorporated herein by reference.

Other features, objects, and advantages of the invention will be apparent from the description of the drawings.

WW, followed by immunoblotting for BIM. Lower panels show the expression of $BIM_{EL}$ and phosphorylated c-Jun.

Figure 1:
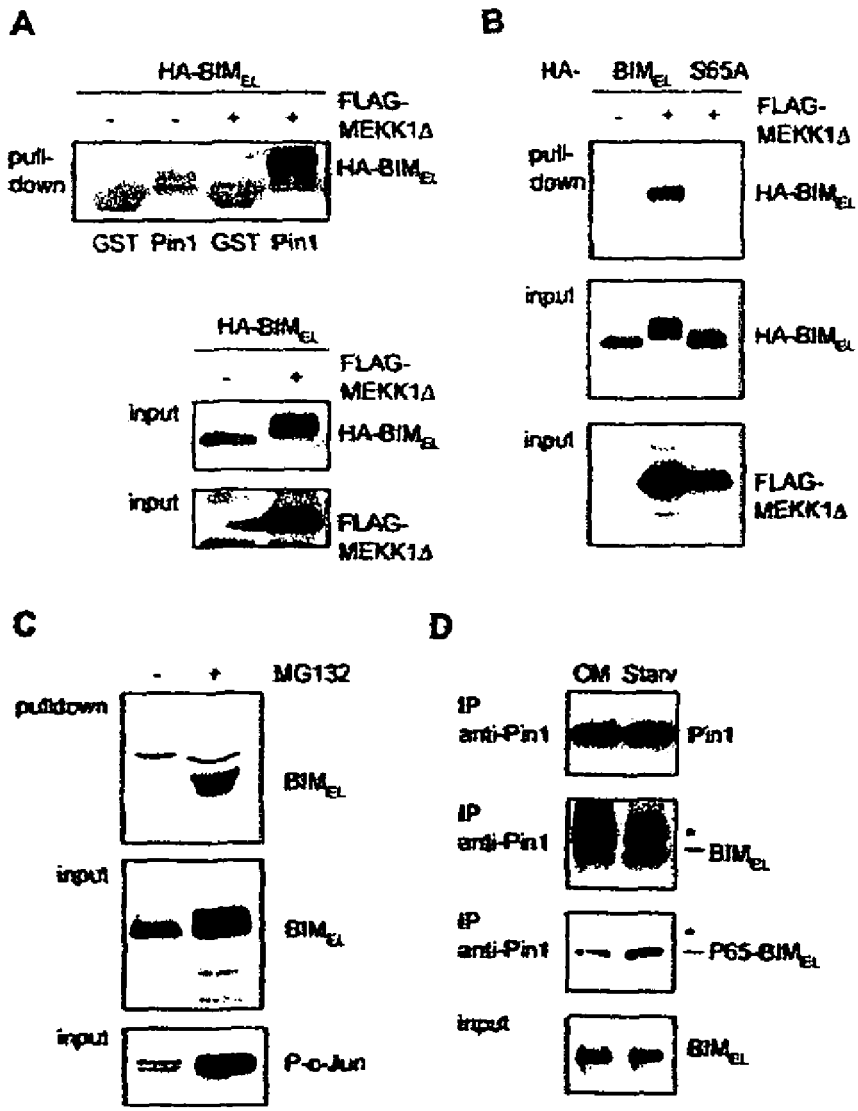
FIG. 1A is a series of immunoblot photographs. Lysates of 293T cells transfected with HA-$BIM_{EL}$ alone or together with FLAG-MEKK1Δ were subjected to a pulldown assay using GST or GST-Pin1, followed by immunoblotting with an anti-HA antibody. Lower panels show the expression of HA-$BIM_{EL}$ and FLAG-MEKK1Δ.
FIG. 1B is a series of immunoblot photographs. Lysates of 293T cells transfected with HA-$BIM_{EL}$ wild type or HA-$BIM_{EL}$ S65A mutant with or without FLAG-MEKK1Δ were subjected to a GST-Pin1 pulldown assay as described in FIG. 1A.
FIG. 1C is a series of immunoblot photographs. Lysates of cerebellar granule neurons untreated or treated for 5 h with 5 μM MG132 were subjected to a pulldown with GST-Pin1

FIG. 1D is a series of immunoblot photographs. Lysates from granule neurons that were kept in conditioned full medium (CM) or starved for 2 h (Starv) were immunoprecipitated with a Pin1 antibody, followed by immunoblotting for Pin1, BIM, and Ser65-phosphorylated BIM. Nonspecific immunoreactivity wgith the IgG light chain is indicated by an asterisk (*). Lower panel shows the expression of $BIM_{EL}$.

Figure 2:
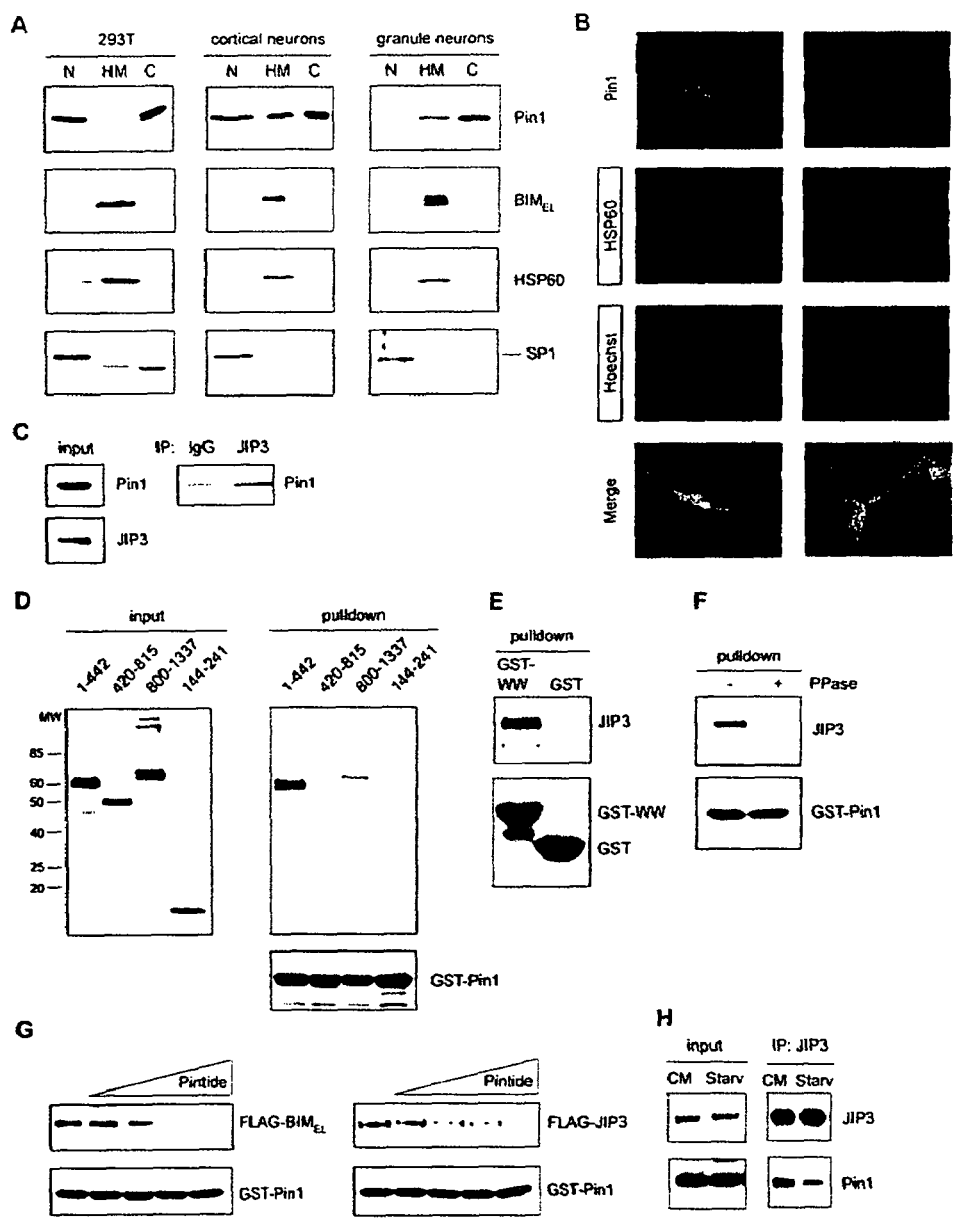

FIG. 2A is a series of immunoblot photographs. Nuclear (N), heavy membrane (HM), and cytosolic (C) fractions prepared from 293T cells, cortical neurons, and cerebellar granule neurons were subjected to immunoblotting for Pin1, BIM, the mitochondrial marker HSP60, and the nuclear marker SP1.

FIG. 2B is a series of immunofluorescent cell stain photographs. Cortical neurons were subjected to indirect immunofluorescence using antibodies to Pin1 and HSP60 and the DNA dye bisbenzimide (Hoechst 33258).

FIG. 2C is a series of immunoblot photographs. Whole brain lysates were immunoprecipitated with a JIP3 antibody or control IgG, followed by immunoblotting for Pin1. Left panels show the expression of Pin1 and JIP3.

FIG. 2D is a series of immunoblot photographs. Lysates of 293T cells transfected with full-length FLAG-JIP3 or FLAG-tagged fragments of JIP3 fragment (1-442, 420-815, 800-1337, and 144-241) were subjected to a GST-Pin1 pulldown, followed by immunoblotting for FLAG and GST. Left panel shows the expression of FLAG-JIP3 fragments.

FIG. 2E is a series of immunoblot photographs. Lysates of granule neurons were subjected to a pulldown assay using GST or GST-Pin1 WW followed by immunoblotting for JIP3 and GST.

FIG. 2F is a series of immunoblot photographs. Lysates of granule neurons were incubated without or with λ phosphatase (PPase), followed by GST-Pin1 pulldown and immunoblotting for JIP3 and GST.

FIG. 2G is a series of immunoblot photographs. Lysates of 293T cells transfected with FLAG-JIP3 or FLAG-$BIM_{EL}$ together with FLAG-MEKK1Δ were subjected to a GST-Pin1 pulldown assay in the presence of increasing amount of Pintide peptide (0, 2.5, 5, 10, 25, 50 mM), followed by immunoblotting for FLAG and GST. Representative immunoblots of three independent experiments are shown.

FIG. 2H is a series of immunoblot photographs. Lysates from granule neurons that were kept in conditioned full medium (CM) or starved for 2 h (Starv) were immunoprecipitated using a JIP3 antibody, followed by immunoblotting for Pin1. Left panels show the expression of JIP3 and Pin1.

Figure 3:
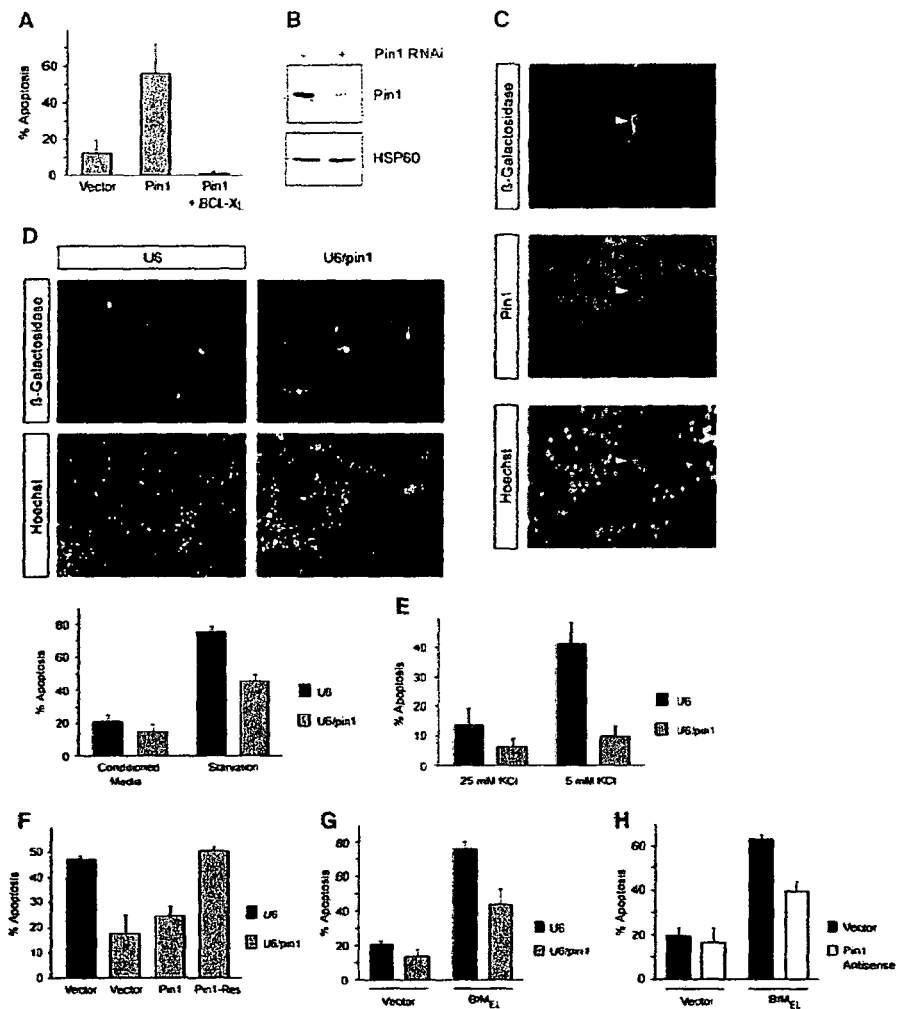

FIG. 3A is a bar graph. Granule neurons were transfected with the control vector or a $BIM_{EL}$ expression plasmid alone or together with a BCL-XL expression plasmid and a β-galactosidase expression vector. Neurons were fixed 40 h after transfection and subjected to indirect immunofluorescence with a β-galactosidase antibody and the DNA dye bisbenzimide (Hoechst 33258). Percentage of apoptosis is represented as mean±SEM. Expression of Pin1 significantly induced apoptosis (n=3; ANOVA; $p<0.05$), but was blocked by coexpression of BCL-XL ($p<0.01$).

FIG. 3B is a series of immunoblot photographs. Lysates of 293T cells transfected with the control vector or Pin1 RNAi plasmid were subjected to immunoblotting for Pin1 and HSP60.

FIG. 3C is a series of immunofluorescent cell stain photographs. Granule neurons transfected with the Pin1 RNAi plasmid and β-galactosidase were subjected to indirect immunofluorescence using antibodies against β-galactosidase and Pin1 and the DNA dye bisbenzimide (Hoechst 33258). Arrowhead points at a transfected neuron with reduced Pin1 immunoreactivity. Endogenous Pin1 was robustly reduced in 50% of Pin1 RNAi-transfected neurons.

FIG. 3D is a series of immunofluorescent cell stain photographs. Granule neurons were transfected with the U6 control vector or U6/pin1 RNAi plasmid together with β-galactosidase. Four days after transfection, neurons were kept in conditioned full medium (CM) or starved for 24 h and subjected to indirect immunofluorescence as in (A). Top panels show representative pictures of the starved neurons. Starvation significantly induced apoptosis in U6-transfected neurons (n=5; ANOVA; $p<0.0001$). Apoptosis upon starvation was significantly reduced in U6/pin1-transfected neurons (n=5; ANOVA; $p<0.0001$).

FIG. 3E is a series of bar graphs. Granule neurons were transfected as in (D). Two days after transfection, neurons that were kept in full medium (BME+5% serum+25 mM KCl) or deprived of KCl for 48 h were fixed and subjected to indirect immunofluorescence as in (A). KCl deprivation significantly induced apoptosis in U6-transfected neurons (n=3; ANOVA; $p<0.005$). Pin1 knockdown significantly protected neurons from KCl deprivation-induced apoptosis (n=3; ANOVA; $p<0.005$).

FIG. 3F is a bar graph. Granule neurons were transfected with the vector control, Pin1, or Pin1-Res plasmid together with the control U6 or U6/pin1 plasmid. Four days after transfection, neurons were starved for 16 h and subjected to indirect immunofluorescence as in (A). Pin1 knockdown significantly reduced apoptosis (n=3; ANOVA; $p<0.005$). Expression of Pin1 failed to rescue the RNAi-induced phenotype, while expression of Pin1-Res significantly reversed the effect of Pin1 RNAi (n=3; ANOVA; $p<0.001$).

FIG. 3G is a bar graph. Granule neurons were transfected with the vector control or a $BIM_{EL}$ expression plasmid together with the control U6 or U6/pin1 RNAi plasmid. Four days after transfection, neurons were starved for 8 h and subjected to indirect immunofluorescence as in (A). Expression of $BIM_{EL}$ significantly induced apoptosis (n=3; ANOVA; $p<0.0001$). $BIM_{EL}$-induced apoptosis was significantly reduced upon Pin1 knockdown (n=3; ANOVA; $p<0.005$).

FIG. 3H is a bar graph. Granule neurons were transfected with the vector control or a $BIM_{EL}$ expression plasmid together with a Pin1 antisense plasmid. Neurons were treated as in (G). Expression of $BIM_{EL}$ significantly induced apoptosis (n=3; ANOVA; $p<0.0005$). Expression of Pin1 antisense RNA significantly reduced $BIM_{EL}$-induced apoptosis (n=3; ANOVA; $p<0.01$).

Figure 4:
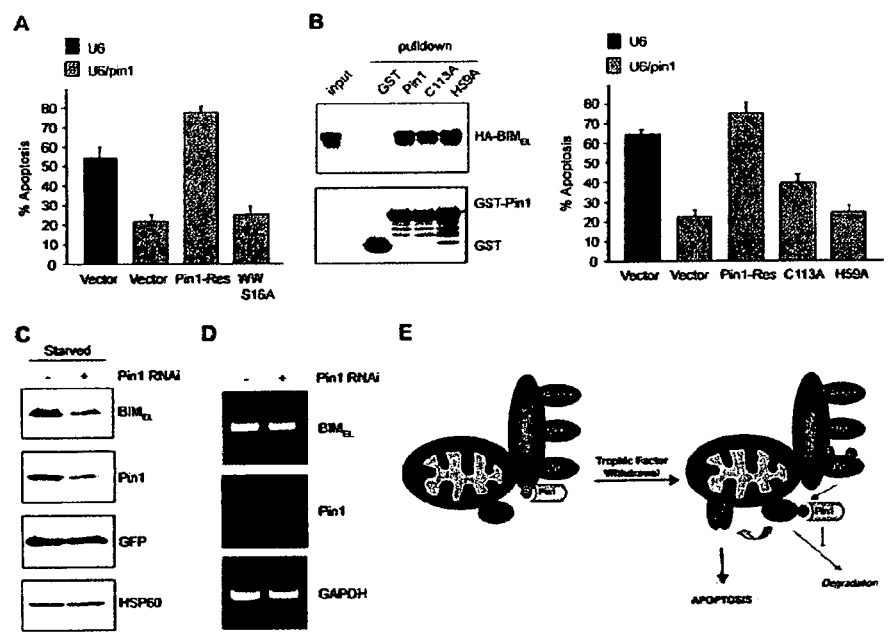

FIG. 4A is a bar graph. Granule neurons were transfected with the vector control, a Pin1-Res, or a Pin1 WW S16A expression plasmid together with the control U6 or U6/pin1 plasmid. Four days after transfection, neurons were starved for 16 h and subjected to indirect immunofluorescence using antibodies against β-galactosidase and Pin1 and the DNA dye bisbenzimide (Hoechst 33258). Pin1 knockdown significantly reduced apoptosis (n=6; ANOVA; $p<0.0001$). Expression of Pin1-Res reversed the RNAi-induced phenotype (n=6; ANOVA; $p<0.0001$), while expression of Pin1 WW S16A had no significant effect.

FIG. 4B is a series of immunoblot photographs and a bar graph. Lysates of 293T cells transfected with HA-$BIM_{EL}$ and FLAG-MEKK1Δ were subjected to a pulldown assay using GST, GST-Pin1, GST-Pin1 C113A, or GSTPin1 H59A, followed by immunoblotting for HA or GST (Left panel). Granule neurons were transfected with the vector control, a Pin1-Res, a Pin1-Res C113A, or a Pin1-Res H59A expression plasmid together with the control U6 or U6/pin1 vector (Right panel). Neurons were treated as in (A). Pin1 knockdown significantly reduced apoptosis (n=3; ANOVA; p<0.0001). Expression of Pin1-Res reversed the Pin1 RNAi-induced phenotype (n=3; ANOVA; p<0.0001), while expression of Pin1-Res C113A and H59A did not significantly affect the Pin1 RNAi-induced survival phenotype.

FIG. 4C is a series of immunoblot photographs. Granule neurons were infected with the vector control or Pin1 RNAi-expressing lentivirus. Four days after infection, neurons were starved for 2 h, lysed, and lysates were subjected to immunoblotting for BIM, Pin1, GFP, and HSP60. Expression of the Pin1 RNAi plasmid significantly reduced Pin1 and $BIM_{EL}$ but not GFP or HSP60 protein levels, as described herein.

FIG. 4D is a series of RT-PCR gel photographs. Granule neurons were infected with the vector control or Pin1 RNAi-expressing lentivirus. Four days after infection, RNA was isolated and subjected to RT-PCR with specific primers to $BIM_{EL}$, Pin1, and GAPDH.

FIG. 4E is a diagram illustrating a model of Pin1's role in JNK-activation of $BIM_{EL}$ in neurons.

Figure 5:
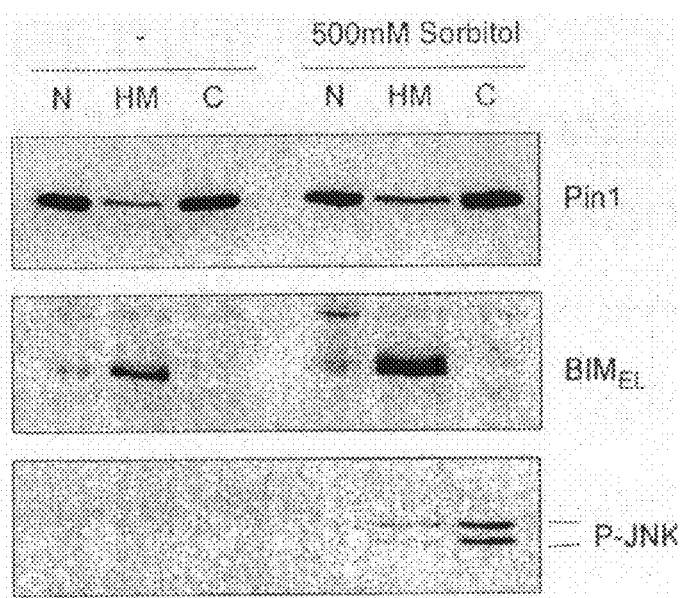

FIG. 5 is a series of immunoblot photographs showing that activation of JNK signaling does not recruit Pin1 to the mitochondria. Nuclear (N), heavy membrane (HM), and cytosolic (C) fractions prepared from 293T cells left untreated or treated with 500 mM sorbitol for 30 min were subjected to immunoblotting using antibodies to Pin1, BIM, and phospho-JNK (P-JNK).

Figure 6:
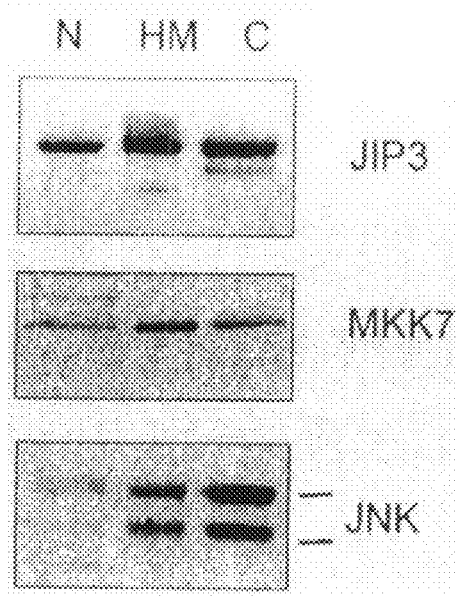

FIG. 6 is a series of immunoblot photographs showing that components of a neuron-specific JNK signaling complex localize to the mitochondria. Nuclear (N), heavy membrane (HM), and cytosolic (C) fractions prepared from cerebellar granule neurons were subjected to immunoblotting using antibodies to JIP3, MKK7, and JNK.

Figures 7A, 7B:
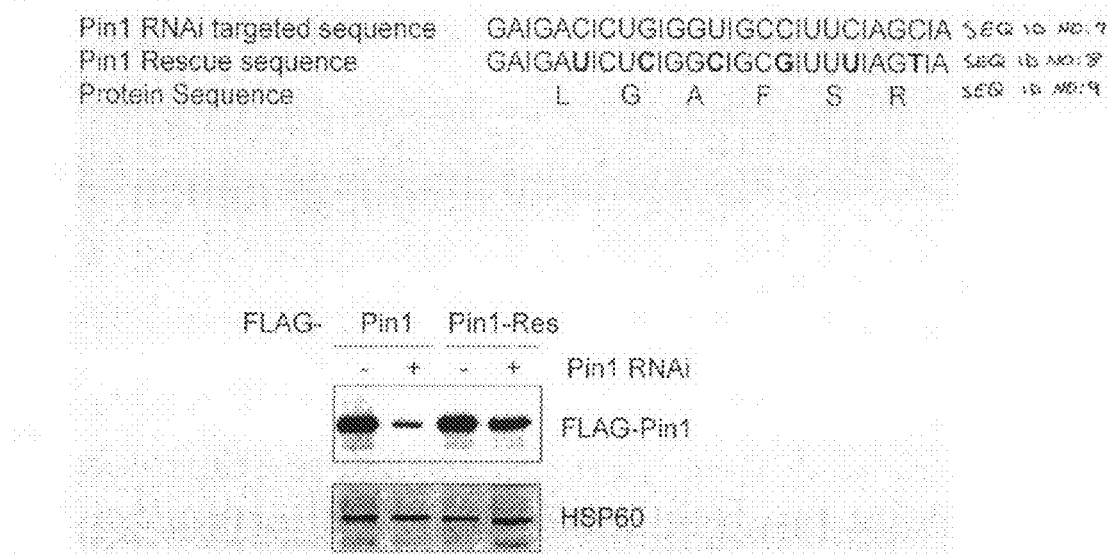

FIG. 7A is a diagram showing Silent base pair mutations in the Pin1-Res construct.

FIG. 7B is a series of immunoblot photographs showing that silent base pair mutations in the Pin1-Rescue (Pin1-Res) expression construct render Pin1-Res insensitive to Pin1 RNAi. Lysates of 293T cells transfected with the control U6 or U6/pin1 plasmid together with a plasmid expressing FLAG-Pin1 or the Pin1 RNAi-insensitive FLAG-Pin1-Res were subjected to immunoblotting with antibodies to FLAG and HSP60.

Figure 8:
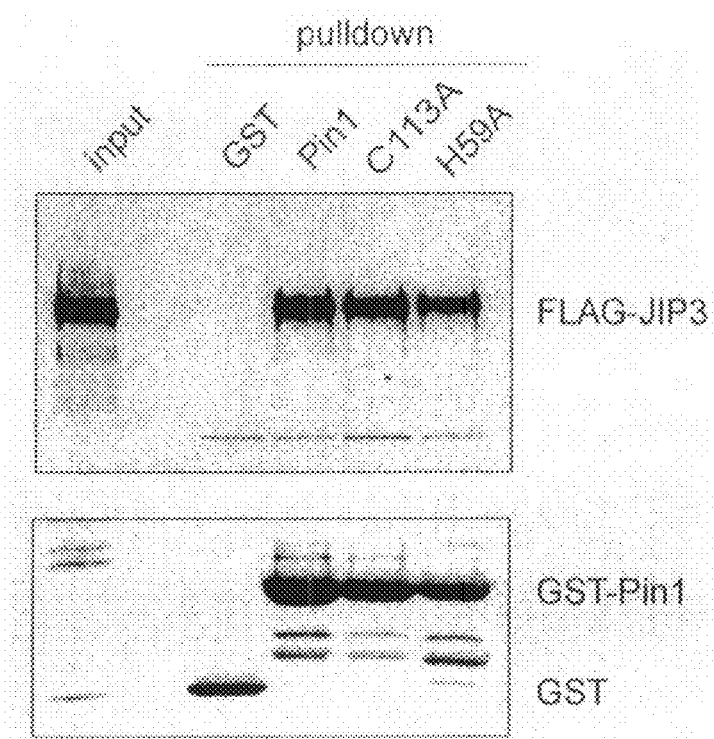

FIG. 8 is a series of immunoblot photographs showing that catalytically impaired Pin1 mutants interact with JIP3. Lysates of 293T cells transfected with FLAG-JIP3 were subjected to a GST-pulldown assay using GST, GST-Pin1, GST-Pin1 C113A (C113A), or GST-Pin1 H59A (H59A), followed by immunoblotting with antibodies to FLAG and GST.

DETAILED DESCRIPTION OF THE INVENTION

The invention is based on the discovery that the prolyl isomerase Pin1 plays a key role in neural apoptosis. In particular, we report that the prolyl isomerase Pin1 interacts with the Ser65-phosphorylated BH3-only protein, $BIM_{EL}$, in neurons, in turn causing neural cell death.

Proteins of the BH3-only family couple apoptotic signals from distinct cellular compartments and signaling pathways to the mitochondrial cell death machinery. The BH3-only protein $BIM_{EL}$ resides at the mitochondria in neurons and mediates neuronal cell death following growth factor deprivation as well as activation of the p75 cell death receptor. These apoptotic stimuli activate c-Jun N-terminal kinase (JNK). JNK in turn phosphorylates $BIM_{EL}$ at the distinct site of Ser65. Whereas phosphorylation of the $BIM_{EL}$ at Ser65 suppresses cell death in non-neural cells, this event triggers apoptosis in neurons. In neurons, Pin1 is enriched at the mitochondrial membrane, where it forms a physical complex with the neuron-specific JNK scaffold protein JIP3. Activation of JNK signaling induces the dissociation of Pin1 from JIP3 and concomitantly promotes Pin1 binding to phosphorylated $BIM_{EL}$. The interaction of Pin1 with phosphorylated $BIM_{EL}$ stabilizes $BIM_{EL}$ and thereby activates neuronal apoptosis. Accordingly, our finding of a neural-specific mechanism of cell death whereby Pin1 couples phosphorylation of BH3-only proteins to activation of the mitochondrial apoptotic machinery provides a rationale for administering inhibitors of Pin1 to reduce or inhibit neural apoptosis, thereby treating or preventing neural disorders. An exemplary inhibitor reduces binding between Pin1 and $BIM_{EL}$.

The experiments described herein were performed using the following Materials and Methods.

Plasmids

Pin1 plasmids were employed. Point mutations in Pin1 were introduced using the QuikChange Site-Directed Mutagenesis Kit (Stratagene), and verified by sequencing. FLAG-tagged JIP3 fragments 1-442, 420-815, 800-1337, and 144-241 were generated by PCR and subcloned into the 3×FLAG CMV-7.1 vector (Sigma). The U6/pin1 RNAi plasmid was designed to specifically target the 21-nucleotide region GAGACCTGGGTGCCTTCAGCA (SEQ ID NO: 1) in Pin1 mouse, rat, and human mRNA. The targeted region in Pin1 showed no significant homology with any other gene by BLAST. The pLentiLox3.7 (pLL3.7) vector was used to generate the Pin1 RNAi lentivirus.

Cell Culture, Transfections, and Infections

Transfections in 293T cells were performed by a calcium phosphate transfection method. Primary cerebellar granule neurons were prepared from 6-day old Long-Evans rats and transfected using a calcium phosphate method as described by Konishi et al. Mol Cell 9: 1005-1016, 2002. Lentivirus was generated in 293T cells by co-transfecting pLL3.7 and viral packaging vectors as described by Rubinson et al., Nat. Genet. 33: 401-406, 2003. Neurons were infected with lentivirus on P6 (8 h after plating) and harvested 4 days later for analysis.

Biochemical Assays

GST-pulldown assays were performed as described by Ryo et al., Mol. Cell 12: 1413-1426, 2003. Immunoprecipitations and subcellular fractionations were performed as described by Konishi et al., Science 303: 1026-1030, 2004. The post-nuclear supernatant was further centrifuged at 10,000 g for 30 min to pellet the mitochondrially-enriched heavy membrane (HM) fraction. Antibodies to BIM (Stressgen); phospho65 BIM antibody (Biosource); HA, HSP60, JIP3, GST (Santa Cruz Biotechnology); FLAG (Sigma); P-c-Jun, MKK7, Pin1 (Cell Signaling); SP1, JNK (Upstate); GFP (Molecular Probes) are available commercially.

Survival Assays in Cerebellar Granule Neurons

Survival assays in granule neurons were done as described by Becker et al., J. Neurosci. 24: 8762-8770, 2004. Cell death was assessed in transfected neurons based on the integrity of neurites and the morphology of the nucleus as determined using the DNA dye bisbenzimide Hoechst 33258 (Sigma). Cell counts were done in a blinded manner (n=100 cells per condition) and analyzed for statistical significance by ANOVA followed by Fisher's protected least significance difference post-hoc test. At least 3 independent experiments were used for statistical analysis.

Therapeutic Agents

An inhibitor of Pin1 is any agent having the ability to reduce the expression or the activity of Pin1 in a cell. The inhibitor preferentially inhibits neural cell death. The control cell is a cell that has not been treated with the Pin1 activator. Pin1 expression or activity is determined by any standard method in the art, including those described herein. Pin1 inhibitors include polypeptides, polynucleotides, small molecule antagonists, or siRNA. For example, a Pin1 inhibitor reduces Pin1 activity by reducing binding between Pin1 and $BIM_{EL}$.

Alternatively, the Pin1 inhibitor is a dominant negative protein or a nucleic acid encoding a dominant negative protein that interferes with the biological activity of Pin1. A dominant negative protein is any amino acid molecule having a sequence that has at least 50%, 70%, 80%, 90%, 95%, or even 99% sequence identity to at least 10, 20, 35, 50, 100, or more than 150 amino acids of the wild type protein to which the dominant negative protein corresponds. For example, a dominant-negative Pin1 has mutation such that it no longer activates downstream pathways. Specifically, a dominant-negative Pin1 binds $BIM_{EL}$ less efficiently than the naturally-occurring Pin1 polypeptide and therefore fails to activate apoptosis.

The dominant negative protein may be administered as an expression vector. The expression vector may be a non-viral vector or a viral vector (e.g., recombinant retrovirus, recombinant lentivirus, recombinant adeno-associated virus, or a recombinant adenoviral vector). Alternatively, the dominant negative protein may be directly administered as a recombinant protein systemically or to the affected area using, for example, microinjection techniques.

The Pin1 inhibitor is an antisense molecule, an RNA interference (siRNA) molecule, a small molecule antagonist that targets Pin1 expression or activity, or a vector that directs production of such inhibitory compositions. By the term "siRNA" is meant a double stranded RNA molecule which prevents translation of a target mRNA. Standard techniques of introducing siRNA into a cell are used, including those in which DNA is a template from which an siRNA RNA is transcribed. The siRNA includes a sense Pin1 nucleic acid sequence, an anti-sense Pin1 nucleic acid sequence or both. Optionally, the siRNA is constructed such that a single transcript has both the sense and complementary antisense sequences from the target gene, e.g., a hairpin. Binding of the siRNA to a Pn1 transcript in the target cell results in a reduction in Pin1 production by the cell. The length of the oligonucleotide is at least 10 nucleotides and may be as long as the naturally-occurring Pin1 transcript. Preferably, the oligonucleotide is 19-25 nucleotides in length. Most preferably, the oligonucleotide is less than 75, 50, 25 nucleotides in length.

Small molecules includes, but are not limited to, peptides, peptidomimetics (e.g., peptoids), amino acids, amino acid analogs, polynucleotides, polynucleotide analogs, nucleotides, nucleotide analogs, organic and inorganic compounds (including heterorganic and organomettallic compounds) having a molecular weight less than about 5,000 grams per mole, organic or inorganic compounds having a molecular weight less than about 2,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. Useful small molecules may reduce Pin1 expression or activity by reducing the interaction between Pin1 and Ser65 phosphorylated $BIM_{EL}$. Inhibitors of prolyl isomerases, e.g., Pin1, include small molecules such as 5-hydroxy-1,4-naphthoquinone (juglone) (Chao et al, 2001, Nucleic Acids Res. 29 (3): 767-773) as well as peptide based compositions such as phosphoSer-cis (or trans) Pro isostere or other conformationally locked pSer-Pros substrate analogues of Pin1. Other Pin1 inhibitors include PiA (2,7-dimethylbenzo[Imn][3,8]phenanthroline-1,3,6,8(2H,7H)-tetrone and PiB(diethyl-1,3,6,8-tetrahydro-1,3,6,8-tetraoxobenzo[Imn][3,8]phenanthroline-2,7-diacetate) (Uchida et al, 2003, Chemistry & Biology 10: 15-24). Daum et al. have reported that aryl indanyl ketones and derivates (compounds (R)-9 and rac-9 pictured below) also inhibit Pin1 (Daum et al. 2006, Angew. Chem. Int. Ed. 45: 7454-7458; hereby incorporated by reference).

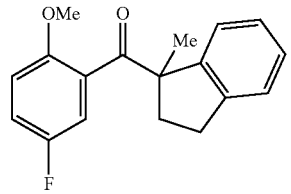

Competitive substrate inhibitors also include peptides based on the Pin1 substrate peptide WFYSPR (SEQ ID NO: 2), which requires a phosphorylated serine residue N-terminal to the proline residue for activity. For example, an inhibitory peptide contains the amino acid sequence YGRKKRRQRRRWFYpSPR (SEQ ID NO: 3) (with a phosphorylated Ser at position 15). Other inhibitory compounds are described in PCT/US99/12544 (hereby incorporated by reference), e.g., a compound with the formaul A-X-R in which A is a radica that mimics the steric and electronic properties of a phosphoserine or phosphothreonine, X is a spacer or absent, and R is a ring structure. Other Pin1 inhibitors include peptides with the sequence Ac-Lys($N^{\epsilon}$-biotinoyl)-Ala-Ala-Bth-D-Thr($PO_3H_2$)-Pip-Nal-Gln-$NH_2$ (SEQ ID NO: 4) or Ac-Phe-D-Thr($PO_3H_2$)-Pip-Nal-Gln-$NH_2$ (SEQ ID NO: 5) (Wildemann et al, 2006, J. Med. Chem. 49: 2147-2150).

A biologically active dose of a Pin1 inhibitor is a dose that will reduce neural apoptosis. Desirably, the Pin1 inhibitor has the ability to reduce the expression or activity of Pin1 in neuronal cells (e.g., granule neurons) by at least 5%, 10%, 20%, 30%, 40%, 50%, 60%, 70%, 80%, 90%, or 100% below untreated control levels. The levels or activity of Pin1 in cells is measured by any method known in the art, including, for example, Western blot analysis, immunohistochemistry, ELISA, and Northern Blot analysis. Alternatively, the biological activity of Pin1 is measured by assessing the expression or activity of any of the molecules involved in Pin1 signaling. The biological activity of Pin1 is determined according to its ability to reduce neural cell apoptosis. Preferably, the agent that reduces the expression or activity of Pin1 can reduce neural cell apoptosis or neurodegeneration by at least 5%, 10%, 20%, 30%, 40%, 50%, 60%, 70%, 80%, 90%, or 100% below untreated control levels. The agent of the present invention is therefore any agent having any one or more of these activities.

Optionally, the subject is administered one or more additional therapeutic regiments. The additional therapeutic regimens may be administered prior to, concomitantly, or subsequent to administration of the Pin1 inhibitor. For example, the Pin1 inhibitor and the additional agent are administered in separate formulations within at least 1, 2, 4, 6, 10, 12, 18, or more than 24 hours apart. Optionally, the additional agent is formulated together with the Pin1 inhibitor. When the additional agent is present in a different composition, different routes of administration may be used. The agent is administered at doses known to be effective for such agent for treating, reducing, or preventing the progression of the neural disorder.

Concentrations of the Pin1 inhibitor and the additional agent depends upon different factors, including means of administration, target site, physiological state of the mammal, and other medication administered. Thus treatment dosages may be titrated to optimize safety and efficacy and is within the skill of an artisan. Determination of the proper dosage and administration regime for a particular situation is within the skill of the art.

Pin1 inhibitors are administered in an amount sufficient to reduce neural apoptosis or neurodegeneration. Such reduction includes the alleviation of one or more of symptoms associated with the neural disorder being treated or prevented. Administration of the Pin1 inhibitor reduces the neurodegeneration associated with the neural disorder or alleviates one or more symptoms associated with the disorder by at least 10%, 20%, 30%, 40%, 50%, 60%, 70%, 80%, 90%, or 100% as compared to an untreated subject.

Treatment is efficacious if the treatment leads to clinical benefit such as, a reduction of the symptoms of a neurologic disorder in the subject. When treatment is applied prophylactically, "efficacious" means that the treatment retards or prevents the neurodegenerative process. Efficacy may be determined using any known method for diagnosing or treating the neural disorder.

Therapeutic Administration

The invention includes administering to a subject a composition that includes a compound that reduces Pin1 expression or activity (referred to herein as an "Pin1 inhibitor" or "therapeutic compound"). As described herein, this inhibitor may reduce binding between Pin1 and $BIM_{EL}$.

An effective amount of a therapeutic compound is preferably from about 0.1 mg/kg to about 150 mg/kg. Effective doses vary, as recognized by those skilled in the art, depending on route of administration, excipient usage, and coadministration with other therapeutic treatments including use of other agents or therapeutic agents for treating, preventing or alleviating a symptom of a neurodegenerative disorder. A therapeutic regimen is carried out by identifying a mammal, e.g., a human patient suffering from (or at risk of developing) a neural disorder, using standard methods.

The pharmaceutical compound is administered to such an individual using methods known in the art. Preferably, the compound is administered orally, rectally, nasally, topically or parenterally, e.g., subcutaneously, intraperitoneally, intrathecally, intramuscularly, and intravenously. The compound is administered prophylactically, or after the detection of the neurologic injury. Compounds are also delivered locally to make direct contact with a site of injury or disease. The compound is optionally formulated as a component of a cocktail of therapeutic drugs to treat the neural disorder. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

The therapeutic compounds described herein are formulated into compositions for other routes of administration utilizing conventional methods. For example, the Pin1 inhibitor is formulated in a capsule or a tablet for oral administration. Capsules may contain any standard pharmaceutically acceptable materials such as gelatin or cellulose. Tablets may be formulated in accordance with conventional procedures by compressing mixtures of a therapeutic compound with a solid carrier and a lubricant. Examples of solid carriers include starch and sugar bentonite. The compound is administered in the form of a hard shell tablet or a capsule containing a binder, e.g., lactose or mannitol, a conventional filler, and a tableting agent. Other formulations include an ointment, suppository, paste, spray, patch, cream, gel, resorbable sponge, or foam. Such formulations are produced using methods well known in the art.

Where the therapeutic compound is a nucleic acid encoding a protein, the therapeutic nucleic acid is administered in vivo to promote expression of its encoded protein, by constructing it as part of an appropriate nucleic acid expression vector and administering it so that it becomes intracellular (e.g., by use of a retroviral vector, by direct injection, by use of microparticle bombardment, by coating with lipids or cell-surface receptors or transfecting agents, or by administering it in linkage to a homeobox-like peptide which is known to enter the nucleus (See, e.g., Joliot, et al., 1991. Proc Natl Acad Sci USA 88:1864-1868), and the like. A nucleic acid therapeutic is introduced intracellularly and incorporated within host cell DNA or remain episomal.

For local administration of DNA, standard gene therapy vectors used. Such vectors include viral vectors, including those derived from replication-defective hepatitis viruses (e.g., HBV and HCV), retroviruses (see, e.g., WO 89/07136; Rosenberg et al., 1990, N. Eng. J. Med. 323(9):570-578), adenovirus (see, e.g., Morsey et al., 1993, J. Cell. Biochem., Supp. 17E,), adeno-associated virus (Kotin et al., 1990, Proc. Natl. Acad. Sci. USA 87:2211-2215,), replication defective herpes simplex viruses (HSV; Lu et al., 1992, Abstract, page 66, Abstracts of the Meeting on Gene Therapy, September 22-26, Cold Spring Harbor Laboratory, Cold Spring Harbor, N.Y.), and any modified versions of these vectors. The invention may utilize any other delivery system which accomplishes in vivo transfer of nucleic acids into eucaryotic cells. For example, the nucleic acids may be packaged into liposomes, e.g., cationic liposomes (Lipofectin), receptor-mediated delivery systems, non-viral nucleic acid-based vectors, erythrocyte ghosts, or microspheres (e.g., microparticles; see, e.g., U.S. Pat. No. 4,789,734; U.S. Pat. No. 4,925,673; U.S. Pat. No. 3,625,214; Gregoriadis, 1979, Drug Carriers in Biology and Medicine, pp. 287-341 (Academic Press,). Naked DNA may also be administered.

DNA for gene therapy can be administered to patients parenterally, e.g., intravenously, subcutaneously, intramuscularly, and intraperitoneally. DNA or an inducing agent is administered in a pharmaceutically acceptable carrier, i.e., a biologically compatible vehicle which is suitable for administration to an animal e.g., physiological saline. A therapeutically effective amount is an amount which is capable of producing a medically desirable result, e.g., a decrease of a Pin1 gene product in a treated animal. Such an amount can be determined by one of ordinary skill in the art. As is well known in the medical arts, dosage for any given patient depends upon many factors, including the patient's size, body surface area, age, the particular compound to be administered, sex, time and route of administration, general health, and other drugs being administered concurrently. Dosages may vary, but a preferred dosage for intravenous administration of DNA is approximately $10^6$ to $10^{22}$ copies of the DNA molecule. Typically, plasmids are administered to a mammal in an amount of about 1 nanogram to about 5000 micrograms of DNA. Desirably, compositions contain about 5 nanograms to 1000 micrograms of DNA, 10 nanograms to 800 micrograms of DNA, 0.1 micrograms to 500 micrograms of DNA, 1 microgram to 350 micrograms of DNA, 25 micrograms to 250 micrograms of DNA, or 100 micrograms to 200 micrograms of DNA. Alternatively, administration of recombinant adenoviral vectors encoding the Pin1 inhibitor into a mammal may be administered at a concentration of at least $10^5$, $10^6$, $10^7$, $10^8$, $10^9$, $10^{10}$, or $10^{11}$ plaque forming unit (pfu).

Pin1 gene products are administered to the patient intravenously in a pharmaceutically acceptable carrier such as physiological saline. Standard methods for intracellular delivery of peptides can be used, e.g. packaged in liposomes. Such methods are well known to those of ordinary skill in the art. It is expected that an intravenous dosage of approximately 1 to 100 moles of the polypeptide of the invention would be administered per kg of body weight per day. The compositions of the invention are useful for parenteral administration, such as intravenous, subcutaneous, intramuscular, and intraperitoneal.

Pin1 inhibitors are effective upon direct contact of the compound with the affected tissue or may alternatively be administered systemically (e.g., intravenously, rectally or orally). The Pin1 inhibitor may be administered intravenously or intrathecally (i.e., by direct infusion into the cerebrospinal fluid). For local administration, a compound-impregnated wafer or resorbable sponge is placed in direct contact with CNS tissue. The compound or mixture of compounds is slowly released in vivo by diffusion of the drug from the wafer and erosion of the polymer matrix. Alternatively, the compound is infused into the brain or cerebrospinal fluid using standard methods. For example, a burr hole ring with a catheter for use as an injection port is positioned to engage the skull at a burr hole drilled into the skull. A fluid reservoir connected to the catheter is accessed by a needle or stylet inserted through a septum positioned over the top of the burr hole ring. A catheter assembly (described, for example, in U.S. Pat. No. 5,954,687) provides a fluid flow path suitable for the transfer of fluids to or from selected location at, near or within the brain to allow administration of the drug over a period of time.

One in the art will understand that the patients treated according to the invention may have been subjected to the tests to diagnose a subject as having a neurologic disorder or may have been identified, without examination, as one at high risk due to the presence of one or more risk factors (e.g., genetic predisposition). Reduction of neurodegenerative symptoms or damage may also include, but are not limited to, alleviation of symptoms (e.g., headaches, nausea, skin rash), diminishment of extent of disease, stabilized (i.e., not worsening) state of disease, delay or slowing of disease progression, and amelioration or palliation of the disease state. Treatment may occur at home with close supervision by the health care provider, or may occur in a health care facility.

Screening Assays

The present invention provides screening methods to identify compounds that can inhibit the expression or activity of Pin1. Useful compounds include any agent that inhibits the biological activity or reduces the cellular level of Pin1. For example, useful compounds are identified by detecting an attenuation of the expression or activity of any of the molecules involved in Pin1 signaling. For example, a useful compound reduces binding between Pin1 and Ser65 phosphorylated $BIM_{EL}$. The screening assays may also identify agents that reduce neural cell apoptosis.

A number of methods are available for carrying out such screening assays. According to one approach, candidate compounds are added at varying concentrations to the culture medium of cells expressing Pin1. Gene expression of Pin1 is then measured, for example, by standard Northern blot analysis, using any appropriate fragment prepared from the nucleic acid molecule of Pin1 as a hybridization probe or by real time PCR with appropriate primers. The level of gene expression in the presence of the candidate compound is compared to the level measured in a control culture medium lacking the candidate molecule. If desired, the effect of candidate compounds may, in the alternative, be measured at the level of Pin1 polypeptide using the same general approach and standard immunological techniques, such as Western blotting or immunoprecipitation with an antibody specific to Pin1 for example. For example, immunoassays may be used to detect or monitor the level of Pin1. Polyclonal or monoclonal antibodies which are capable of binding to Pin1 may be used in any standard immunoassay format (e.g., ELISA or RIA assay) to measure the levels of Pin1. Pin1 can also be measured using mass spectroscopy, high performance liquid chromatography, spectrophotometric or fluorometric techniques, or combinations thereof.

As a specific example, mammalian cells (e.g., rodent cells) that express a nucleic acid encoding Pin1 are cultured in the presence of a candidate compound (e.g., a peptide, polypeptide, synthetic organic molecule, naturally occurring organic molecule, nucleic acid molecule, or component thereof). Cells may either endogenously express Pin1 or may alternatively be genetically engineered by any standard technique known in the art (e.g., transfection and viral infection) to overexpress Pin1. The expression level of Pin1 is measured in these cells by means of Western blot analysis and subsequently compared to the level of expression of the same protein in control cells that have not been contacted by the candidate compound. A compound which promotes a decrease in the level of Pin1 activity as a result of reducing its synthesis or biological activity is considered useful in the invention.

Alternatively, the screening methods of the invention may be used to identify candidate compounds that decrease the biological activity of Pin1 by reducing neural cell apoptosis by at least 10%, 20%, 30%, 40%, 50%, 60%, 70%, 80%, 90%, 95%, or 100% relative to an untreated control. As another alternative, candidate compounds are identified for their ability to reduce binding between Pin1 and $BIM_{EL}$. A candidate compound may be tested for its ability to reduce such binding in neural cells that naturally express Pin1 and $BIM_{EL}$ or after transfection with cDNA for Pin1 and $BIM_{EL}$, or in cell-free solutions containing Pin1 and $BIM_{EL}$, as described further below. The effect of a candidate compound on the binding or activation of $BIM_{EL}$ can be tested by radioactive and non-radioactive binding assays, competition assays, and receptor signaling assays.

Given its ability to decrease the biological activity of Pin1, such a molecule may be used, for example, as a therapeutic agent to treat, reduce, or prevent a neural disorder, or alternatively, to alleviate one or more symptoms associated with such a disorder. As a specific example, a candidate compound may be contacted with two proteins, the first protein being a polypeptide substantially identical to Pin1 and the second protein being $BIM_{EL}$ (i.e., a protein that binds the Pin1 polypeptide under conditions that allow binding). According to this particular screening method, the interaction between these two proteins is measured following the addition of a candidate compound. A decrease in the binding of Pin1 to $BIM_{EL}$ following the addition of the candidate compound (relative to such binding in the absence of the compound) identifies the candidate compound as having the ability to inhibit the interaction between the two proteins, and thereby having the ability to reduce Pin1 activity. The screening assay of the invention may be carried out, for example, in a cell-free system or using a yeast two-hybrid system. If desired, one of the proteins or the candidate compound may be immobilized on a support as described above or may have a detectable group.

Alternatively, or in addition, candidate compounds may be screened for those which specifically bind to and thereby inhibit Pin1. The efficacy of such a candidate compound is dependent upon its ability to interact with Pin1. Such an interaction can be readily assayed using any number of standard binding techniques and functional assays. For example, a candidate compound may be tested in vitro for interaction and binding with Pin1 and its ability to modulate neural cell apoptosis may be assayed by any standard assays (e.g., those described herein).

For example, a candidate compound that binds to Pin1 may be identified using a chromatography-based technique. For example, a recombinant Pin1 may be purified by standard techniques from cells engineered to express Pin1 and may be immobilized on a column. Alternatively, the naturally-occurring Pin1 may be immobilized on a column. A solution of candidate compounds is then passed through the column, and a compound specific for Pin1 is identified on the basis of its ability to bind to Pin1 and be immobilized on the column. To isolate the compound, the column is washed to remove non-specifically bound molecules, and the compound of interest is then released from the column and collected. Compounds isolated by this method (or any other appropriate method) may, if desired, be further purified (e.g., by high performance liquid chromatography).

Screening for new inhibitors and optimization of lead compounds may be assessed, for example, by assessing their ability to modulate Pin1 activity using standard techniques. Compounds which are identified as binding to Pin1 with an affinity constant less than or equal to 10 mM are considered particularly useful in the invention.

Potential therapeutic agents include organic molecules, peptides, peptide mimetics, polypeptides, and antibodies that bind to a nucleic acid sequence encodes Pin1 or a Pin1 peptide and thereby inhibit or extinguish their activity. Inhibitory agents also include small molecules that bind to and occupy domains of Pin1 or $BIM_{EL}$ that interact with each other. Other potential agents include antisense molecules.

This invention is based in part on the experiments described in the following examples. These examples are provided to illustrate the invention and should not be construed as limiting.

Pin1 Interacts with Phosphorylated $BIM_{EL}$ in Vitro and in Vivo.

The phosphorylation of $BIM_{EL}$ at Ser65 triggers apoptosis specifically in neurons but not in non-neural cells. A critical regulatory post-phosphorylation event is the prolyl isomerization of proteins at sites of proline-dependent phosphorylation. A major function of Pin1 is to drive cells through mitosis in proliferating cells. Pin1 is also highly expressed in the nervous system. To assess whether Pin1 binds to Ser65-phosphorylated $BIM_{EL}$ in vitro, we used a GST pulldown assay. We expressed $BIM_{EL}$ in 293T cells alone or together with a constitutively active form of the kinase MEKK1 (MEKK1Δ), an upstream activator of JNK. Expression of MEKK1Δ results in the robust phosphorylation of $BIM_{EL}$ at Ser65, which is reflected by a mobility shift of $BIM_{EL}$ (FIG. 1A). Recombinant GST-Pin1, but not GST, specifically co-precipitated phosphorylated but not unphosphorylated $BIM_{EL}$ from cell lysates (FIG. 1A). The Pin1-$BIM_{EL}$ interaction was dependent on phosphorylation of $BIM_{EL}$ at Ser65, as GST-Pin1 did not bind to a $BIM_{EL}$ mutant in which Ser65 was replaced with alanine that was co-expressed with MEKK1Δ (FIG. 1B). In other experiments, we tested if a recombinant GST fusion protein containing the WW domain of Pin1 associates with $BIM_{EL}$. The WW domain of Pin1 interacts specifically with phosphoSer/Thr-Pro motifs. GST-Pin1 WW protein was incubated with lysates of cerebellar granule neurons that were untreated or treated with the proteasome inhibitor MG132, which activated JNK signaling as reflected by the phosphorylation of c-Jun and $BIM_{EL}$ (FIG. 1C). GST-Pin1 WW interacted with phosphorylated but not unphosphorylated $BIM_{EL}$ (FIG. 1C). Together, these results show that Pin1 interacts with Ser65-phosphorylated $BIM_{EL}$ in neural cells.

We next determined whether endogenous Pin1 and $BIM_{EL}$ interact in neurons. Endogenous $BIM_{EL}$ co-immunoprecipitated with Pin1 in lysates of granule neurons that were starved for two hours to activate JNK signaling but not in lysates of neurons kept under survival conditions (conditioned medium, CM) (FIG. 1D). $BIM_{EL}$ protein that coimmunoprecipitated with Pin1 was phosphorylated at Ser65 as determined by immunoblotting with a phospho-Ser65-specific antibody (FIG. 1D). Thus, Pin1 interacts with JNK-induced Ser65-phosphorylated $BIM_{EL}$ selectively in neurons compared to non-neural cells.

Pin1 is Localized at the Mitochondria in Neurons and Associates with the Neuron-Specific JNK Signaling Scaffold Protein JIP3

We next determined the subcellular site of the Pin1-$BIM_{EL}$ interaction in neurons. $BIM_{EL}$ resides at the mitochondria in neurons (FIG. 2A). Pin1 however has been reported to primarily localize to the cell nucleus in non-neural cells. To address how Pin1 might function immediately downstream of $BIM_{EL}$ in neurons, we characterized the expression of Pin1 in fractionated lysates of neurons and non-neural cells. In 293T and COS cells, Pin1 localized predominantly to the nuclear and cytosolic fraction (FIG. 2A). The heavy membrane fraction however contained significantly lower amounts of Pin1 (FIG. 2A). Surprisingly, a significant amount of Pin1 in neurons was found in the heavy membrane fraction that also contains $BIM_{EL}$ and the mitochondrial marker HSP60 (FIG. 2A). Thus, in neurons the heavy membrane fraction contained either a similar amount or more Pin1 than the nuclear fraction (FIG. 2A). We also analyzed the subcellular localization of Pin1 by confocal microscopy in neurons. Pin1 immunoreactivity was present at the mitochondria in cortical and granule neurons (FIG. 2B). Together, these results indicate that Pin1 is enriched at the mitochondria specifically in neurons but not in nonneural cells.

We next determined the mechanism by which Pin1 is tethered to the mitochondria in neurons and thus facilitates the interaction of Pin1 with Ser65-phosphorylated $BIM_{EL}$. We ruled out that activation of JNK signaling might recruit Pin1 to the mitochondria independently of cell type since robust activation of the JNK signaling pathway by treatment of 293T cells with sorbitol did not lead to appreciable changes in the subcellular localization of Pin1 (FIG. 5). Since JNK signaling cascades are organized on scaffold proteins that coordinate activation and specificity of signal transduction, we next considered the possibility that Pin1 might be enriched at the mitochondria in neurons together with a component of a neuron-specific JNK signaling complex. The JNK-interacting protein 3 (JIP3) scaffold protein is selectively expressed in neurons. A substantial portion of JIP3 and the associated proteins MKK7 and JNK were found to reside at the mitochondria-enriched heavy membrane fraction in neurons, where they co-localized with Pin1 and $BIM_{EL}$ (FIGS. 2A and 6). Furthermore, Pin1 specifically co-immunoprecipitated with JIP3 in whole brain lysates (FIG. 2C). These findings support the possibility that Pin1 interacts with a neuron-specific JNK signaling complex at the mitochondria in neurons. We next carried out structure-function analyses to determine the regions of JIP3 and Pin1 that associate with each other. Pin1 interacted robustly with the N-terminal domain of JIP3 (aa 1-442) and only weakly with the region of JIP3 that interacts with MLK3 and MKK7 (aa 420-815) or the C-terminal region of JIP3 (aa 800-1337) (FIG. 2D). The N-terminal region of JIP3 encompasses the JNK binding domain (JBD) of JIP3 (aa 207-216). However, Pin1 failed to interact with a JIP3 region spanning residues 144-241 (FIG. 2D), indicating that Pin1 binds to JIP3 at sites that are distinct from the JBD.

In other experiments, we found that endogenous JIP3 in granule neurons robustly interacted with recombinant GST-Pin1 or GST-Pin1 WW in vitro (FIG. 2E, 2F), suggesting that Pin1 interacts with phosphorylated JIP3. Although GST-Pin1 coprecipitated with JIP3 from control lysates, GST-Pin1 failed to co-precipitate JIP3 from lysates treated with phosphatase (FIG. 2F). Thus, similar to $BIM_{EL}$, JIP3 interacts with Pin1 in a phosphorylation-dependent manner. In additional GST pulldown assays, increasing amounts of an optimal Pin1-binding peptide (Pintide) (WFYpSPRLKK; SEQ ID NO: 6) similarly disrupted the interaction of Pin1 with JIP3 and $BIM_{EL}$ in a dose-dependent manner (FIG. 2G). Since the WW domain contains a single binding pocket for Pintide, our results suggest that phosphorylated JIP3 and $BIM_{EL}$ bind to the same phosphoprotein-binding pocket of the Pin1 WW domain.

To determine whether the binding of Pin1 to JIP3 is regulated by an apoptotic stimulus, we measured the interaction of endogenous Pin1 and JIP3 in granule neurons that were left in full medium (conditioned medium, CM) or that were starved for two hours. Pin1 co-immunoprecipitated with JIP3 in full medium (FIG. 2H). However, activity and growth factor withdrawal, as well as exposure of neurons to other JNK activating stimuli including MG132 and hydrogen peroxide, led to a decrease in the interaction of Pin1 and JIP3 (FIG. 2H). Accompanying the dissociation of Pin1 and JIP3, there was increased association of Pin1 with $BIM_{EL}$ (FIG. 1D). Together, our findings indicate that Pin1 associates with a neuron-specific JIP3 scaffold complex at the mitochondria. Upon a JNK-activating stress stimulus, Pin1 is released from JIP3 and associates with Ser65-phosphorylated $BIM_{EL}$ at the mitochondria.

Pin1 Contributes to Survival Factor Withdrawal-Induced and $BIM_{EL}$-Induced Apoptosis in Neurons The interaction of Pin1 with Ser65-phosphorylated $BIM_{EL}$ in neurons led us to investigate whether Pin1 might mediate the ability of Ser65-phosphorylated $BIM_{EL}$ to induce apoptosis specifically in neurons. We first determined the role of Pin1 in apoptosis of granule neurons. Expression of exogenous Pin1 in granule neurons significantly induced cell death (FIG. 3A). Pin1-induced apoptosis was blocked by coexpression of BCL-XL or upon inhibition of caspases (FIG. 3A), indicating that Pin1 promotes cell death through the cell-intrinsic apoptotic machinery.

To assess the role of endogenous Pin1 in neuronal apoptosis, we employed a vector-based RNA interference (RNAi) method. The expression of Pin1 hairpin RNAs (hpRNAs) effectively reduced endogenous Pin1 expression in 293T cells and primary neurons (FIG. 3B, 3C). We next determined the effect of Pin1 knockdown on apoptosis induced in neurons by withdrawal of growth factors and the inhibition of neuronal activity. Inhibition of neuronal activity, achieved by lowering the concentrations of potassium chloride, or the withdrawal of both activity and growth factors induced apoptosis in control U6 plasmid-transfected neurons (FIGS. 3D, 3E). However, Pin1 knockdown significantly protected neurons from cell death under both apoptotic stimuli (FIGS. 3D, 3E). Under these apoptotic conditions, Pin1 hpRNA-expressing neurons had robust neurites and intact nuclei compared to neurons transfected with the control plasmid (FIG. 3D). Pin1 knockdown also protected neurons from apoptosis induced upon expression of MEKK1Δ. These results indicate that Pin1 is required for growth factor and activity withdrawal-dependent and JNK-induced neuronal cell death.

To ensure specificity of the Pin1 knockdown-induced phenotype, we performed a rescue experiment. We generated an expression construct encoding a Pin1 rescue that is insensitive to the Pin1 RNAi (Pin1-Res). Pin1 knockdown reduced the expression of Pin1, but failed to effectively reduce the levels of Pin1-Res (FIG. 6). Expression of Pin1-Res but not Pin1 encoded by wild type cDNA reversed the protective effect of Pin1 RNAi against apoptosis in neurons (FIG. 3F). Thus, the Pin1 RNAi-triggered protection from neuronal apoptosis is the result of specific knockdown of Pin1 rather than off-target effects of Pin1 RNAi.

Experiments were carried out to determine whether Pin1 is required for $BIM_{EL}$ to induce cell death in neurons. The expression of $BIM_{EL}$ on its own potently induced apoptosis in neurons, knockdown of Pin1 significantly inhibited $BIM_{EL}$-induced apoptosis (FIG. 3G). Expression of antisense Pin1 RNA also significantly reduced $BIM_{EL}$-induced cell death (FIG. 3H). These results indicate that Pin1 is involved in $BIM_{EL}$-induced apoptosis preferentially in neurons.

Pin1 Isomerase Activity is Required for Neuronal Apoptosis and Stabilizes $BIM_{EL}$ Protein in Neurons Having identified that Pin1 is an important mediator of apoptosis downstream of JNK-$BIM_{EL}$ signaling in neurons, we next investigated the mechanism underlying Pin1-induced neuronal cell death. Based on the observation that Pin1-Res reverses the Pin1 RNAi-induced survival phenotype, structure-function analyses of Pin1 in the background of Pin1 knockdown were carried out. Pin1 contains an amino-terminal WW domain that binds to specific phosphoSer/Thr-Pro motifs and a carboxyl-terminal enzymatic peptidyl prolyl isomerase (PPI) domain that catalyzes the cis-trans isomerization of the phosphoSer/Thr-Pro bonds. To determine whether binding of phosphoproteins through its WW domain is sufficient for the apoptotic function of Pin1, we expressed a Pin1 WW domain that contains an additional mutation (S16A), thereby allowing Pin1 to bind tightly to its substrates. As the Pin1 hpRNAs target the C-terminal PPI domain of Pin1, the Pin1 WW S16A mutant is insensitive to the Pin1 RNAi. In contrast to Pin1-Res, expression of Pin1 WW S16A failed to rescue the Pin1 RNAi-induced survival phenotype in granule neurons, indicating that the WW domain is not sufficient for the apoptotic function of Pin1 in neurons (FIG. 4A).

To assess the role of the PPI domain in Pin1-mediated cell death, we generated two catalytically impaired Pin1-Res constructs by mutating the critical catalytical sites C113A and H59A. The C113A and H59A mutations significantly reduce Pin1's PPI activity without affecting Pin1-substrate binding.

We expressed the Pin1-Res mutants C113A and H59A in the background of Pin1 RNAi. In contrast to Pin1-Res, both Pin1-Res mutants failed to reverse the Pin1 RNAi-induced survival phenotype in neurons (FIG. 4B). The C113A or H59A mutation had little or no effect on the binding of Pin1 to $BIM_{EL}$ or JIP3 (FIGS. 4B and 8). These results indicate that a functional PPI domain is required for Pin1-mediated neuronal apoptosis.

The requirement of the PPI domain for Pin1-mediated neuronal cell death suggests that a conformational change in the Pin1 substrate $BIM_{EL}$ may be required for its function in neuronal apoptosis. This raises the question of how the binding and consequent isomerization of Ser65-phosphorylated $BIM_{EL}$ by Pin1 might induce $BIM_{EL}$-dependent apoptosis in neurons. Phosphorylation of $BIM_{EL}$ at Ser65 by ERK1/2 in nonneural cells is reported to promote degradation of $BIM_{EL}$ by the proteasome. To assess the effect of Pin1 on $BIM_{EL}$ protein levels, we induced knockdown of Pin1 in granule neurons using a Pin1 RNAi lentivirus. Four days after lentiviral infection, neurons were starved for two hours to activate JNK signaling. Pin1 protein levels were significantly reduced upon induction of Pin1 RNAi (65±3% reduction compared to control vector-infected neurons; n=3; ANOVA; p<0.0001) (FIG. 4C). $BIM_{EL}$ protein levels were also significantly reduced in the Pin1 RNAi-infectedneurons (46±1.5% reduction; n=3; ANOVA; p<0.0001) (FIG. 4C). However, the levels of co-expressed GFP and endogenous HSP60 remained unaltered. Although Pin1 knockdown led to a reduction in $BIM_{EL}$ protein levels, $BIM_{EL}$ mRNA levels remained unchanged upon Pin1 knockdown (FIG. 4D). These results suggest that Pin1 stabilizes $BIM_{EL}$ protein levels in neurons. In other experiments in which we fractionated lysates of neurons following lentiviral-mediated RNAi, we found that while Pin1 knockdown reduced the amount of $BIM_{EL}$, the mitochondrial localization of $BIM_{EL}$ remained unaltered. These findings indicate that the presence of Pin1 in a neuron-specific mitochondrial JNK signaling complex allows Pin1 to bind $BIM_{EL}$ after its phosphorylation by JNK, promoting a conformational change in $BIM_{EL}$, and thereby protecting Ser65-phosphorylated $BIM_{EL}$ from proteasomal degradation in neurons (see model in FIG. 4E).

The data define a mechanism by which JNK-induced phosphorylation of the BH3-only protein $BIM_{EL}$ at Ser65 triggers apoptosis specifically in neurons. Our results show that the prolyl isomerase Pin1 interacts with Ser65-phosphorylated $BIM_{EL}$ in neurons. A significant proportion of Pin1 in neurons but not in non-neural cells is localized at the mitochondrial membrane, where $BIM_{EL}$ resides. Pin1 associates with the neuron-specific JNK signaling scaffold protein JIP3. Upon exposure of neurons to apoptotic stimuli that induce JNK signaling, Pin1 dissociates from JIP3 and concomitantly interacts with JNK-phosphorylated $BIM_{EL}$. The interaction of Pin1 with Ser65-phosphorylated $BIM_{EL}$ stabilizes $BIM_{EL}$ and thereby promotes neuronal apoptosis. These findings define a neuron-specific cell death mechanism, whereby Pin1 mediates activation of the mitochondrial cell death machinery.

These results illustrate that the phosphorylation of $BIM_{EL}$ at Ser65 elicits strikingly distinct responses depending on cell type, leading to apoptosis in neurons and cell survival in proliferating non-neural cells. The phosphorylation of $BIM_{EL}$ at Ser65 is mediated by ERK1/2 in non-neural cells and thought to lead to the ubiquitin-dependent proteasomal degradation of $BIM_{EL}$. Our findings however indicate that the binding of Pin1 to Ser65-phosphorylated $BIM_{EL}$ and its consequent isomerization in neurons may act as a molecular switch that protects $BIM_{EL}$ from ubiquitination and degradation (FIG. 4E). Thus, Pin1's function in neuronal apoptosis appears to be conferred by its distinct subcellular localization in neurons. Our results indicate that the selective enrichment of Pin1 at the mitochondrial membrane in neurons may result from the interaction of Pin1 with the JNK signaling scaffold protein JIP3. The JIP proteins and associated components of the JNK signaling pathway play key roles in neuronal apoptosis. Among the JIP proteins, JIP3 is expressed in a neuron-specific pattern, and within neurons robust amounts of JIP3 and other components of the JNK signaling pathway are localized at the mitochondrial membrane (FIG. 6). Thus, the association of Pin1 with JIP3 provides the basis for the participation of the ubiquitously expressed Pin1 in activation of the mitochondrial apoptotic machinery specifically in neurons.

The identification of Pin1's interaction with JIP3 has important ramifications for both Pin1 and JIP3 function in neurons. Studies of JIP3 in *Drosophila, C. elegans*, and mice point to functions of JIP3 in kinesin-dependent anterograde axonal transport. JIP3 also interacts with the dynactin/dynein motor complex and thus engages in retrograde transport of JNK signaling in response to nerve injury. Our findings provides support for Pin1 as a link between JIP3-propagated axonal injury signals and the activation of the cell death machinery. JIP3 and Pin1 have an intimate colocalization pattern in subcellular fractions in addition to the mitochondria in neurons. The JIP3 signaling complex participates in the regulation of other Pin1 functions in the nervous system, by counteracting the degenerative effects of hyperphosphorylated tau on the neuronal cytoskeleton. In addition to its role downstream of Ser65-phosphorylated $BIM_{EL}$, Pin1 has a more general role in neuronal cell death, e.g., in dividing cells, Pin1 promotes cell cycle progression by acting on substrates of the mitotic kinase Cdc2. Cdc2 induces apoptosis in neurons and Pin1 may contribute to Cdc2-induced cell death in neurons.

Our results provide a basis for manipulating the expression or activity of Pin1 at the mitochondrial membrane and its interactions with JIP3 in the treatment of neurologic diseases.

What is claimed is:

1. A method of treating cerebral ischemic disease by administering directly to a neural cell of a mammal an RNA interfering molecule that specifically targets and reduces the level or activity of human prolyl isomerase Pin1.

2. The method of claim 1, wherein said cerebral ischemic disease is stroke.

3. The method of claim 1, wherein said neural cell is a granule neuron.

4. The method of claim 1, wherein said mammal is further administered a second therapeutic regimen.

5. The method of claim 1, wherein said RNA interfering molecule specificallytargets GAGACCTGGGTGCCTTCAGCA (SEQ ID NO: 1)in Pin 1 mRNA.

6. The method of claim 1, wherein said RNA interfering molecule is administered intrathecally.

* * * * *